(12) United States Patent
Fiandaca et al.

US010718021B2

(10) Patent No.: US 10,718,021 B2
(45) Date of Patent: Jul. 21, 2020

(54) GENETIC MARKERS FOR MEMORY LOSS

(71) Applicants: GEORGETOWN UNIVERSITY, Washington, DC (US); UNIVERSITY OF ROCHESTER, Rochester, NY (US)

(72) Inventors: Massimo S. Fiandaca, Millersville, MD (US); Mark E. Mapstone, Pittsford, NY (US); Yuriy Gusev, North Bethesda, MD (US); Howard J. Federoff, Bethesda, MD (US)

(73) Assignees: GEORGETOWN UNIVERSITY, Washington, DC (US); UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/312,856

(22) PCT Filed: May 28, 2015

(86) PCT No.: PCT/US2015/032910
§ 371 (c)(1),
(2) Date: Nov. 21, 2016

(87) PCT Pub. No.: WO2015/184107
PCT Pub. Date: Dec. 3, 2015

(65) Prior Publication Data
US 2017/0183733 A1 Jun. 29, 2017

Related U.S. Application Data

(60) Provisional application No. 62/003,666, filed on May 28, 2014, provisional application No. 62/004,357, filed on May 29, 2014.

(51) Int. Cl.
*A61K 38/00* (2006.01)
*C12Q 1/68* (2018.01)
*G01N 33/567* (2006.01)
*C12Q 1/6883* (2018.01)
*C12Q 1/6876* (2018.01)

(52) U.S. Cl.
CPC ......... *C12Q 1/6883* (2013.01); *C12Q 1/6876* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2010/0021913 A1 1/2010 Alkon et al.
2012/0283114 A1 11/2012 Cohen et al.

FOREIGN PATENT DOCUMENTS

WO 2013/066764 A2 5/2013
WO 2014/046871 A1 3/2014

OTHER PUBLICATIONS

International Search Report issued in the corresponding International Application No. PCT/US2015/032910 dated Sep. 1, 2015.

*Primary Examiner* — Olga N Chernyshev
(74) *Attorney, Agent, or Firm* — Grimes & Yvon LLP (57) ABSTRACT

The present invention relates to methods of determining if a subject has an increased risk of suffering from memory impairment. The methods comprise analyzing the gene expression profile from peripheral blood leukocytes taken from the subject and comparing the value of the subject's gene expression profile with the value of a normal gene expression profile. A change in the value of the subject's gene expression profile, above or below normal values is indicative that the subject has an increased risk of suffering from memory impairment compared to a normal individual.

5 Claims, 1 Drawing Sheet

US 10,718,021 B2

GENETIC MARKERS FOR MEMORY LOSS

STATEMENT REGARDING FEDERALLY SPONSORED RESEARCH OR DEVELOPMENT

This invention was made with government support under grant number R01 AG030753 awarded by the National Institutes of Health and under contract number W81XWH-09-1-0107 awarded by the Department of Defense. The government has certain rights in the invention.

BACKGROUND OF THE INVENTION

Field of the Invention

The present invention relates to methods of determining if a subject has an increased risk of suffering from memory impairment. The methods comprise analyzing the gene expression profile from peripheral blood leukocytes taken from the subject and comparing the value of the subject's gene expression profile with the value of a normal gene expression profile. A change in the value of the subject's gene expression profile, above or below normal values is indicative that the subject has an increased risk of suffering from memory impairment compared to a normal individual.

Background of the Invention

Alzheimer's disease (AD) is a neurodegenerative disorder characterized by a progressive dementia that insidiously and inexorably robs older adults of their memory and other cognitive abilities. The prevalence of AD is expected to double every 20 years from 35.6 million individuals worldwide in 2010 to 115 million affected individuals by 2050. There is no cure and current therapies are unable to slow progression of the disease.

Early detection of the at-risk population (preclinical), or those in the initial symptomatic stages (prodromal, or mild cognitive impairment, MCI) of AD, may present opportunities for more successful therapeutic intervention, or even disease prevention by interdicting the neuropathological cascade that is ultimately characterized by the deposition of extracellular β-amyloid (Aβ) and accumulation of intracellular fibrils of hyperphosphorylated microtubule associated protein tau (MAPT or tau) within the brain. Biomarkers for early disease, including cerebrospinal fluid (CSF) tau and Aβ levels, structural and functional magnetic resonance imaging (MRI), and the recent use of brain positron emission tomography (PET) amyloid imaging, are of limited use as widespread screening tools since they provide diagnostic options that are either invasive (i.e., require lumbar puncture), time-consuming (i.e., several hours in a scanner for most comprehensive imaging protocols), or expensive, or have been primarily validated in comparisons between normal subjects and those with the disease. No current blood-based biomarkers can detect incipient dementia with the required sensitivity and specificity during the preclinical stages. Continued interest in blood-based biomarkers remains because these specimens are obtained using minimally invasive, rapid, and relatively inexpensive methods. With recent technological advances in 'omics' technologies and systems biology analytic approaches, the comprehensive bioinformatic analyses of blood-based biomarkers may not only yield improved accuracy in predicting those at risk, but may also provide new insights into the underlying mechanisms and pathobiological networks involved in AD and possibly herald the development of new therapeutic strategies.

The preclinical interval resulting in MCI or AD is known to be variable, multifactorial, and extends for at least 7-10 years prior to the emergence of clinical signs (prodromal or manifest disease). In the absence of accurate and easily obtained biomarkers, multimodal neurocognitive testing remains the most accurate, standardized, and widely used pre-mortem screening method to determine the presence or absence of clinical MCI or AD. The utility of strict cognitive assessment for preclinical stages of MCI or AD is limited, however, as this approach is not only time-consuming but is expected, by definition, to be normal in preclinical subjects. Neuropsychological testing is able to quantitatively delineate specific brain alterations from normal, such as memory, attention, language, visuoperceptual, and executive functions, which are typically not affected in individuals during the preclinical stages. Thus, information obtained from multiple diagnostic studies will probably be most useful in defining the MCI/AD preclinical stages, including neuropsychological testing and some form(s) of biomarker(s). While CSF and neuroimaging have been used to define preclinical MCI/AD to date, their clinical utility as screening tools for asymptomatic individuals is not established.

SUMMARY OF THE INVENTION

The present invention relates to methods of determining if a subject has an increased risk of suffering from memory impairment. The methods comprise analyzing the gene expression profile from peripheral blood leukocytes taken from the subject and comparing the value of the subject's gene expression profile with the value of a normal gene expression profile. A change in the value of the subject's gene expression profile, above or below normal values is indicative that the subject has an increased risk of suffering from memory impairment compared to a normal individual.

DETAILED DESCRIPTION OF THE INVENTION

Figure 1:
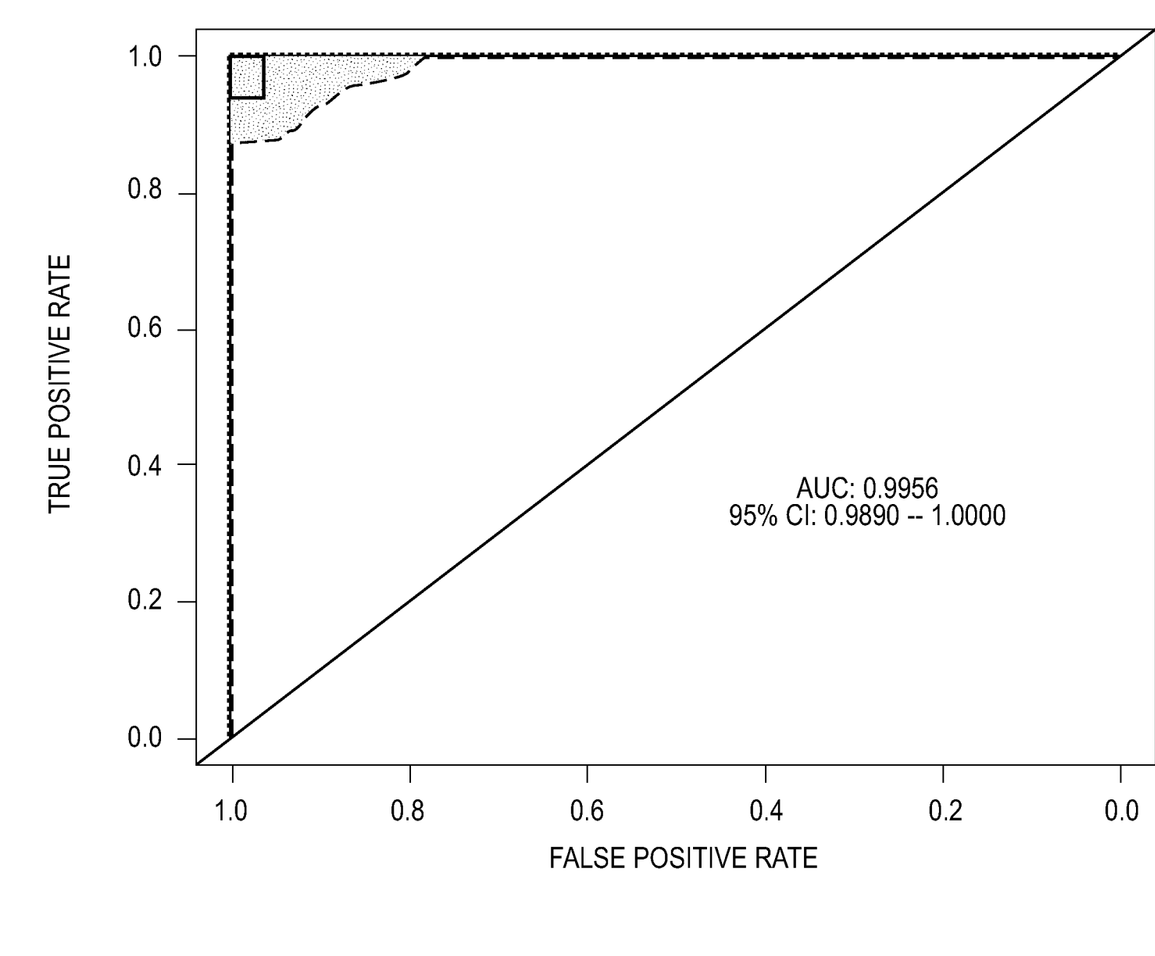
FIG. 1 depicts an area under the curve (AUC) analysis using the 25 differentially expressed genes identified using the materials and methods described herein.

The present invention relates to methods of determining if a subject has an increased risk of suffering from memory impairment. The methods comprise analyzing the gene expression profile from peripheral blood leukocytes taken from the subject and comparing the value of the subject's gene expression profile with the value of a normal gene expression profile. A change in the value of the subject's gene expression profile, above or below normal values is indicative that the subject has an increased risk of suffering from memory impairment compared to a normal individual.

As used herein, the term subject or "test subject" indicates a mammal, in particular a human or non-human primate. The test subject may or may not be in need of an assessment of a predisposition to memory impairment. For example, the test subject may have a condition or may have been exposed to injuries or conditions that are associated with memory impairment prior to applying the methods of the present invention. In another embodiment, the test subject has not been identified as a subject that may have a condition or may have been exposed to injuries or conditions that are associated with memory impairment prior to applying the methods of the present invention.

As used herein, the phrase "memory impairment" means a measureable or perceivable decline or decrease in the subject's ability to recall past events. As used herein, the term "past events" includes both recent (new) events (short-term memory) or events further back in time (long-term memory). In one embodiment, the methods are used to assess an increased risk of short-term memory impairment. In another embodiment, the methods are used to assess an increased risk in long-term memory impairment. The memory impairment can be age-related memory impairment. The memory impairment may also be disease-related memory impairment. Examples of disease-related memory impairment include but are not limited to Alzheimer's Disease, Parkinson's Disease, Multiple Sclerosis, Huntington's Disease, Pick's Disease, Progressive Supranuclear Palsy, Brain Tumor(s), Head Trauma, and Lyme Disease to name a few. In one embodiment, the memory impairment is related to amnestic mild cognitive impairment (aMCI). In another embodiment, the memory impairment is related to Alzheimer's Disease. The root cause of the memory impairment is not necessarily critical to the methods of the present invention. The measureable or perceivable decline in the subject's ability to recall past events may be assessed clinically by a health care provider, such as a physician, physician's assistant, nurse, nurse practitioner, psychologist, psychiatrist, hospice provider, or any other provider that can assess a subject's memory. The measureable or perceivable decline in the subject's ability to recall past events may be assessed in a less formal, non-clinical manner, including but not limited to the subject himself or herself, acquaintances of the subject, employers of the subject and the like. The invention is not limited to a specific manner in which the subject's ability to recall past events is assessed. In fact, the methods of the invention can be implemented without the need to assess a subject's ability to recall past events. Of course, the methods of the present invention may also include assessing the subject's ability to assess past events one or more times, both before determining the subject's gene expression profile after determining the subject's gene expression profile at least one time.

In one embodiment, the decline or decrease in the ability to recall past events is relative to each individual's ability to recall past events prior to the diagnosed decrease or decline in the ability to recall past events. In another embodiment, the decline or decrease in the ability to recall past events is relative to a population's (general, specific or stratified) ability to recall past events prior to the diagnosed decrease or decline in the ability to recall past events.

As used herein, the term means "increased risk" is used to mean that the test subject has an increased chance of developing or acquiring memory impairment compared to a normal individual. The increased risk may be relative or absolute and may be expressed qualitatively or quantitatively. For example, an increased risk may be expressed as simply determining the subject's gene expression profile and placing the patient in an "increased risk" category, based upon previous population studies. Alternatively, a numerical expression of the subject's increased risk may be determined based upon the gene expression profile. As used herein, examples of expressions of an increased risk include but are not limited to, odds, probability, odds ratio, p-values, attributable risk, relative frequency, positive predictive value, negative predictive value, and relative risk.

For example, the correlation between a subject's gene expression profile and the likelihood of suffering from memory impairment may be measured by an odds ratio (OR) and by the relative risk (RR). If $P(R^+)$ is the probability of developing memory impairment for individuals with the risk profile (R) and $P(R^-)$ is the probability of developing memory impairment for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the gene expression profile frequencies of the study.

The attributable risk (AR) can also be used to express an increased risk. The AR describes the proportion of individuals in a population exhibiting memory impairment due to a specific member of the gene expression profile. AR may also be important in quantifying the role of individual components (specific member) in disease etiology and in terms of the public health impact of the individual marker. The public health relevance of the AR measurement lies in estimating the proportion of cases of memory impairment in the population that could be prevented if the profile or individual component were absent. AR may be determined as follows: $AR=P_E(RR-1)/(P_E(RR-1)+1)$, where AR is the risk attributable to a profile or individual component of the profile, and $P_E$ is the frequency of exposure to a profile or individual component of the profile within the population at large. RR is the relative risk, which can be approximated with the odds ratio when the profile or individual component of the profile under study has a relatively low incidence in the general population.

In one embodiment, the increased risk of a patient can be determined from p-values that are derived from association studies. Specifically, associations with specific profiles can be performed using regression analysis by regressing the gene expression profile with memory impairment. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's apolipoprotein E (ApoE) genotype to name a few.

Increased risk can also be determined from p-values that are derived using logistic regression. Binomial (or binary) logistic regression is a form of regression used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring. These analyses are conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and non-parametric analysis.

As used herein, the phrase "gene expression profile" means the combination of a subject's gene expression levels in cells, e.g., leukocytes, isolated from the subject's peripheral blood. Specifically, the phrase "gene expression profile" means a collection of measurements, such as but not limited to a quantity or concentration, for expression of individual genes taken from the RNA extracts of a test sample of the subject. Examples of test samples or sources of components for the RNA extracts for the gene expression profile include, but are not limited to, cells from biological fluids, such as but not limited to whole blood, cerebrospinal fluid, urine, amniotic fluid, lymph fluids, and various external secretions of the respiratory, intestinal and genitourinary tracts, tears, saliva, milk, and the like. Test samples to be assayed also include but are not limited to tissue specimens including normal and abnormal tissue. In specific embodiments, RNA or protein extracts from cells that are contained in the samples are used to generate a gene expression profile.

Techniques to assay levels of individual components of the gene expression profile from test samples are well known to the skilled technician, and the invention is not limited by the means by which the components are assessed. In one embodiment, levels of the individual components of the gene expression profile are assessed using RNA sequencing or quantitative arrays, and the like. To determine the level of gene expression, complete RNA sequencing information can be, but is not necessarily, used to determine quantitative levels of gene expression, and thereby a gene expression profile. In addition, to determine levels of gene expression, it is not necessary that an entire RNA transcript, which represents a "gene product," be present or fully sequenced. In other words, determining levels of, for example, a fragment of an RNA transcript from a gene being analyzed may be sufficient to conclude or assess that the individual gene being analyzed is up- or down-regulated. Similarly, if, for example, arrays or blots are used to determine gene expression levels, the presence/absence/strength of a detectable signal will be sufficient to assess levels of gene expression without the need to sequencing an RNA transcript.

The assessment of the levels of the individual components of the gene expression profile can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

To assess levels of the individual components of the gene expression profile, a sample is taken from the subject. The sample may or may not processed prior assaying levels of the components of the gene expression profile. For example, whole blood may be taken from an individual and the blood sample may be processed, e.g., centrifuged or otherwise processed, to isolate specific components, e.g., plasma, serum, red blood cells, platelets, exosomes, or leukocytes, from the blood. The blood specimen may be collected specifically for RNA analysis (via a PAXgene tube). The sample may or may not be stored, e.g., frozen, prior to processing or analysis.

Individual components of the gene expression profile include but are not limited to SART3, SMARCB1, EXO1, CKAP2L, RGPD2, RBFOX2, SKIL, STYX, SORBS2, LYPLA1, CHGA, PXDNL, SGMS2, OBSCN, RAPGEF3, SPRY2, FAM98C, ABLIM3, MARCH4, SCLY, GATAD2A, STAG2, DTNA, HSD17B4, PML Those of skill in the art will recognize the specific identity of each constituent listed based upon the nomenclature above. The differentially expressed genes are in Table 1. In one embodiment, the differentially expressed genes are upregulated compared to normal levels. In another embodiment, one, two, three, four, five, six, seven, eight, nine, 10, 11, 12, 13, 14, 15, 16, 17, 18, 19, 20, 21, 22, 23, 24 or 25 of the genes are upregulated over normal levels.

The levels of up or down regulation compared to normal levels can vary. In one embodiment, the expression levels of any one or more of the genes is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 times or more or less, depending on the gene, above or below (up- or down-regulated compared to) the normal levels.

TABLE 1

List of Top 25 Differentially Expressed Genes for use in the Gene Expression Profile

| Rank_SVM-RFE | Gene | Symbol | Entrez Gene Name | Location | Type(s) |
|---|---|---|---|---|---|
| 1 | SART3 | SART3 | squamous cell carcinoma antigen recognized by T cells 3 | Nucleus | other |
| 2 | SMARCB1 | SMARCB1 | SWI/SNF related, matrix associated, actin dependent regulator of chromatin, subfamily b, member 1 | Nucleus | transcription regulator |
| 3 | EXO1 | EXO1 | exonuclease 1 | Nucleus | enzyme |
| 4 | CKAP2L | CKAP2L | cytoskeleton associated protein 2-like | Cytoplasm | other |
| 5 | RGPD2 | RGPD3 (includes others) | RANBP2-like and GRIP domain containing 5 | Nucleus | other |
| 6 | RBFOX2 | RBFOX2 | RNA binding protein, fox-1 homolog (C. elegans) 2 | Nucleus | transcription regulator |
| 7 | SKIL | SKIL | SKI-like oncogene | Nucleus | transcription regulator |
| 8 | STYX | STYX | serine/threonine/tyrosine interacting protein | Cytoplasm | phosphatase |
| 9 | SORBS2 | SORBS2 | sorbin and SH3 domain containing 2 | Plasma Membrane | other |

TABLE 1-continued

List of Top 25 Differentially Expressed Genes for use in the Gene Expression Profile

| Rank_SVM-RFE | Gene | Symbol | Entrez Gene Name | Location | Type(s) |
|---|---|---|---|---|---|
| 10 | LYPLA1 | LYPLA1 | lysophospholipase I | Cytoplasm | enzyme |
| 11 | CHGA | CHGA | chromogranin A (parathyroid secretory protein 1) | Cytoplasm | other |
| 12 | PXDNL | PXDNL | peroxidasin homolog (Drosophila)-like | Extracellular Space | enzyme |
| 13 | SGMS2 | SGMS2 | sphingomyelin synthase 2 | Plasma Membrane | enzyme |
| 14 | OBSCN | OBSCN | obscurin, cytoskeletal calmodulin and titin-interacting RhoGEF | Cytoplasm | kinase |
| 15 | RAPGEF3 | RAPGEF3 | Rap guanine nucleotide exchange factor (GEF) 3 | Nucleus | other |
| 16 | SPRY2 | SPRY2 | sprouty homolog 2 (Drosophila) | Plasma Membrane | other |
| 17 | FAM98C | FAM98C | family with sequence similarity 98, member C | Other | other |
| 18 | ABLIM3 | ABLIM3 | actin binding LIM protein family, member 3 | Cytoplasm | other |
| 19 | MARCH4 | MARCH4 | membrane-associated ring finger (C3HC4) 4, E3 ubiquitin protein ligase | Cytoplasm | enzyme |
| 20 | SCLY | SCLY | selenocysteine lyase | Cytoplasm | enzyme |
| 21 | GATAD2A | GATAD2A | GATA zinc finger domain containing 2A | Nucleus | transcription regulator |
| 22 | STAG2 | STAG2 | stromal antigen 2 | Nucleus | other |
| 23 | DTNA | DTNA | dystrobrevin, alpha | Plasma Membrane | other |
| 24 | HSD17B4 | HSD17B4 | hydroxysteroid (17-beta) dehydrogenase 4 | Cytoplasm | enzyme |
| 25 | PML | PML | promyelocytic leukemia | Nucleus | transcription regulator |

For the purposes of the present invention the gene expression profile comprises at least two, three, four, five, six, seven, eight, nine, 10, 11, 12, 13, 14, 15, 16, 17, 18, 19, 20, 21, 22, 23, 24 or 25 genes listed herein. If two genes are used in generating the gene expression profile, any combination of two genes listed above can be used. If three genes are used in generating the gene expression profile, any combination of three genes listed above can be used. If four genes are used in generating the gene expression profile, any combination of four genes listed above can be used. If five genes are used in generating the gene expression profile, any combination of five genes listed above can be used. If six genes are used in generating the gene expression profile, any combination of six genes listed above can be used. If seven genes are used in generating the gene expression profile, any combination of seven genes listed above can be used. If eight genes are used in generating the gene expression profile, any combination of eight genes listed above can be used. If nine genes are used in generating the gene expression profile, any combination of nine genes listed above can be used. If ten genes are used in generating the gene expression profile, any combination of ten genes listed above can be used. If 11 genes are used in generating the gene expression profile, any combination of 11 genes listed above can be used. If 12 genes are used in generating the gene expression profile, any combination of 12 genes listed above can be used. If 13 genes are used in generating the gene expression profile, any combination of 13 genes listed above can be used. If 14 genes are used in generating the gene expression profile, any combination of 14 genes listed above can be used. If 15 genes are used in generating the gene expression profile, any combination of 15 genes listed above can be used. If 16 genes are used in generating the gene expression profile, any combination of 16 genes listed above can be used. If 17 genes are used in generating the gene expression profile, any combination of 17 genes listed above can be used. If 18 genes are used in generating the gene expression profile, any combination of 18 genes listed above can be used. If 19 genes are used in generating the gene expression profile, any combination of 19 genes listed above can be used. If 20 genes are used in generating the gene expression profile, any combination of 20 genes listed above can be used. If 21 genes are used in generating the gene expression profile, any combination of 21 genes listed above can be used. If 22 genes are used in generating the gene expression profile, any combination of 22 genes listed above can be used. If 23 genes are used in generating the gene expression profile, any combination of 23 genes listed above can be used. If 24 genes are used in generating the gene expression profile, any combination of 24 genes listed above can be used. Of course, all 25 of the genes listed herein can be used to generate the gene expression profile.

The subject's gene expression profile is compared to the profile that is deemed to be a normal gene expression profile. To establish the gene expression profile of a normal individual, an individual or group of individuals may be first assessed for their ability to recall past events to establish that the individual or group of individuals has a normal or acceptable ability memory. Once established, the gene expression profile of the individual or group of individuals can then be determined to establish a "normal gene expression profile." In one embodiment, a normal gene expression profile can be ascertained from the same subject when the subject is deemed to possess normal cognitive abilities and no signs (clinical or otherwise) of memory impairment. In one embodiment, a "normal" gene expression profile is assessed in the same subject from whom the sample is taken prior to the onset of measureable, perceivable or diagnosed memory impairment. That is, the term "normal" with respect to a gene expression profile can be used to mean the subject's baseline gene expression profile prior to the onset of memory impairment. The gene expression profile can then be reassessed periodically and compared to the subject's baseline gene expression profile. Thus, the present invention also include methods of monitoring the progression of memory impairment in a subject, with the methods comprising determining the subject's gene expression profile more than once over a period of time. For example, some embodiments of the methods of the present invention will comprise determining the subject's gene expression profile two, three, four, five, six, seven, eight, nine, 10 or even more times over a period of time, such as a year, two years, three, years, four years, five years, six years, seven years, eight years, nine years or even 10 years or longer. The methods of monitoring a subject's risk of having memory impairment would also include embodiments in which the subject's gene expression profile is assessed during and after treatment of memory impairment. In other words, the present invention also includes methods of monitoring the efficacy of treatment of memory impairment by assessing the subject's gene expression profile over the course of the treatment and after the treatment. The treatment may be any treatment designed to increase a subject's ability to recall past events, i.e., improve a subject's memory.

In another embodiment, a normal gene expression profile is assessed in a sample from a different subject or patient (from the subject being analyzed) and this different subject does not have or is not suspected of having memory impairment. In still another embodiment, the normal gene expression profile is assessed in a population of healthy individuals, the constituents of which display no memory impairment. Thus, the subject's gene expression profile can be compared to a normal gene expression profile generated from a single normal sample or a gene expression profile generated from more than one normal sample.

Of course, measurements of the individual components, e.g., expression levels, of the normal gene expression profile can fall within a range of values, and values that do not fall within this "normal range" are said to be outside the normal range. These measurements may or may not be converted to a value, number, factor or score as compared to measurements in the "normal range." For example, a measurement for a specific gene that is expressed at levels below the normal range, may be assigned a value or −1, −2, −3, etc., depending on the scoring system devised.

In one embodiment, the "gene expression profile value" can be a single value, number, factor or score given as an overall collective value to the individual genetic components of the profile, or to the categorical components, i.e., the enzymatic portion of the gene expression profile. For example, if each component is assigned a value, such as above, the gene expression value may simply be the overall score of each individual or categorical value. For example, if 10 components are used to generate the enzymatic portion of the gene expression profile and five of the components are assigned values of "−2" and five are assigned values of "−1," the enzymatic portion of the gene expression profile value in this example would be −15, with a normal value being, for example, "0." Continuing the example, if 9 components are used to generate the inflammatory reaction portion of the gene expression profile and five of the components are assigned values of "2" and four are assigned values of "−1," the inflammatory reaction portion of the gene expression profile in this example would be 6, with a normal value being, for example "0." In this manner, the overall gene expression profile value could be useful single number or score, the actual value or magnitude of which could be an indication of the actual risk of memory impairment, e.g., the "more negative" the value, the greater the risk of memory impairment.

In another embodiment the "gene expression profile value" can be a series of values, numbers, factors or scores given to the individual components or genes of the overall profile. In another embodiment, the "gene expression profile value" may be a combination of values, numbers, factors or scores given to genetic components of the profile as well as values, numbers, factors or scores collectively given to a group of components. For example, the measurements of the enzymatic genetic potion in the profile may be grouped into one composite score, individual genes associated with inflammation may be grouped into another composite score and differential expression of anti-inflammatory genes may be grouped into another score. In another example, the gene expression profile value may comprise or consist of individual values, number, factors or scores for specific genes or genetic components.

In another embodiment individual gene expression values from a list of genes can be used to develop a single score, such as a "combined gene expression index," which may utilize weighted scores from the individual gene expression values reduced to a diagnostic number value. The combined gene expression index may also be generated using non-weighted scores from the individual gene expression values. When the "combined gene expression index" exceeds (or is less than) a specific threshold level, the individual has a high risk of memory impairment, whereas the maintaining a normal range value of the "combined gene expression index" would indicate a low or minimal risk of memory impairment. In this embodiment, the threshold value would be set by the combined gene expression index from normal subjects.

In another embodiment, the value of the gene expression profile can be the collection of data from the individual expression levels and need not be converted to a scoring system, such that the "gene expression profile value" is a collection of the individual expression levels of the individual components of the profile.

In specific embodiments, a subject is diagnosed of having an increased risk of suffering from memory impairment if the expression levels of 25, 24, 23, 22, 21, 20, 19, 18, 17, 16, 15, 14, 13, 12, 11, 10, nine, eight, seven, six, five, four, three, two or even one of the genes described herein are at abnormal levels, e.g., all of the genes are expressed at higher or lower levels than normal levels.

TABLE 2

Levels of Differential Expression of Certain Genes

| Gene Name | Gene Regulation | Log Ratio | False Discovery Rate (q-value) | p-value |
| --- | --- | --- | --- | --- |
| SART3 | down | −4.396 | 3.13E−02 | 9.41E−05 |
| SMARCB1 | down | −6.302 | 1.23E−02 | 1.72E−05 |
| EXO1 | down | −8.285 | 1.21E−02 | 1.65E−05 |
| CKAP2L | down | −7.276 | 6.07E−03 | 5.33E−06 |
| RGPD2 | down | −6.187 | 3.97E−02 | 1.79E−04 |
| RBFOX2 | down | −4.484 | 4.64E−02 | 2.52E−04 |
| SKIL | up | 1.421 | 5.16E−02 | 3.05E−04 |

TABLE 2-continued

Levels of Differential Expression of Certain Genes

| Gene Name | Gene Regulation | Log Ratio | False Discovery Rate (q-value) | p-value |
|---|---|---|---|---|
| STYX | up | 1.425 | 5.54E−02 | 3.60E−04 |
| SORBS2 | down | −3.834 | 7.23E−02 | 6.11E−04 |
| LYPLA1 | up | 1.246 | 1.37E−02 | 2.33E−05 |
| CHGA | down | −2.708 | 9.14E−02 | 9.50E−04 |
| PXDNL | down | −4.397 | 1.69E−05 | 2.52E−09 |
| SGMS2 | up | 1.125 | 5.77E−02 | 3.93E−04 |
| OBSCN | up | 10.413 | 3.97E−02 | 1.77E−04 |
| RAPGEF3 | down | −2.124 | 1.12E−02 | 1.44E−05 |
| SPRY2 | up | 7.211 | 8.20E−02 | 7.94E−04 |
| FAM98C | up | 7.413 | 4.60E−02 | 2.45E−04 |
| ABLIM3 | up | 8.464 | 7.55E−02 | 6.72E−04 |
| MARCH4 | down | −3.717 | 2.50E−02 | 6.13E−05 |
| SCLY | up | 10.526 | 6.78E−03 | 6.33E−06 |
| GATAD2A | down | −0.778 | 4.26E−02 | 2.05E−04 |
| STAG2 | up | 12.462 | 5.01E−03 | 3.55E−06 |
| DTNA | up | 8.447 | 1.18E−02 | 1.54E−05 |
| HSD17B4 | up | 10.515 | 4.22E−02 | 1.99E−04 |
| PML | up | 12.77 | 6.85E−04 | 2.69E−07 |

If it is determined that a subject has an increased risk of memory impairment, the attending health care provider may subsequently prescribe or institute a treatment program. In this manner, the present invention also provides for methods of screening individuals as candidates for treatment of memory impairment. The attending healthcare worker may begin treatment, based on the subject's gene expression profile, before there are perceivable, noticeable or measurable signs of memory impairment in the individual.

Similarly, the invention provides methods of monitoring the effectiveness of a treatment for memory impairment. Once a treatment regimen has been established, with or without the use of the methods of the present invention to assist in a diagnosis of memory impairment, the methods of monitoring a subject's gene expression profile over time can be used to assess the effectiveness of a memory impairment treatment. Specifically, the subject's gene expression profile can be assessed over time, including before, during and after treatments for memory impairment. The gene expression profile can be monitored, with, for example, a decline in the values of the profile over time being indicative that the treatment may not be as effective as desired.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety

EXAMPLES

Example 1

Neurocognitive Methods

A total of 525 volunteers participated in this study as part of the Rochester/Orange County Aging Study (R/OCAS), an ongoing natural history study of cognition in community-dwelling older adults. Briefly, participants were followed with yearly cognitive assessments and blood samples were collected following an overnight fast and withholding of all medications. At baseline and each yearly visit, participants completed assessments in such as activities in daily living, memory complaints, signs and symptoms of depression, and were administered a detailed cognitive assessment.

For this study, data from the cognitive tests were used to classify participants into groups for biomarker discovery. Standardized scores (Z-scores) were derived for each participant on each cognitive test and the composite Z-scores were computed for five cognitive domains (attention, executive, language, memory, visuoperceptual) (Table 2).

TABLE 3

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Wechsler Memory Scale-III Forward Digit Span (WMS-III FDS) | Wechsler Memory Scale-III Backward Digit Span (WMS-III BDS) | 1-min Category fluency (Animals) | Hooper Visual Organization Test (HVOT) | Rey Auditory Verbal Learning Test Learning (RAVLT Learning) |
| Trail Making Test-Part A (TMT-A) | Trail Making Test-Part B (TMT-B) | Boston Naming Test 60-Item version (BNT-60) | | Rey Auditory Verbal Learning Test Retrieval (RAVLT Retrieval) Rey Auditory Verbal Learning Test Retention (RAVLT Recognition) |

Normative data for Z-score calculations were derived from the performance of the participants on each of the cognitive tests adjusted for age, education, sex, and visit. To reduce the effect of cognitively impaired participants on the mean and SD, age-, education-, sex, and visit-adjusted residuals from each domain Z-score model were robustly standardized to have median 0 and robust SD=1, where the robust SD=IQR/1.35, as 1.35 is the IQR (Inter-Quartile Range) of a standard normal distribution.

The participants were then categorized into groups of incident aMCI or early AD (combined into one category aMCI/AD), cognitively normal control (NC), and those who converted to MCI or AD over the course of the study (Converters) based on these composite scores. Impairment was defined as a Z-score 1.35 SD below the cohort median. All participants classified as aMCI met recently revised criteria for the amnestic subtype of MCI. Other behavioral phenotypes of MCI were excluded to concentrate on the amnestic form, which most likely represents nascent Alzheimer's pathology. All early AD participants met recently revised criteria for probable Alzheimer's disease with impairment in memory and at least one other cognitive domain. For the MCI and early AD groups, scores on the measures of memory complaints (MMQ) and activities of daily living (PGC-IADL) were used to corroborate research definitions of these states. All Converters had non-impaired memory at entry to the study ($Z_{mem} \geq -1.35$), developed memory impairment over the course of the study ($Z_{mem} \leq -1.35$) and met criteria for the above definitions of aMCI or AD. To enhance the specificity of the biomarker analyses, NC participants in this study were conservatively defined with $Z_{mem} \pm 1$ SD of the cohort median rather than simply $\geq -1.35$, and all other Z-scores $\geq -1.35$ SD.

For each subject, $Z_{mem}$(last), $Z_{att}$(last), $Z_{exe}$(last), $Z_{lan}$(last), and $Z_{vis}$(last) were defined as the age-gender-education-visit-adjusted robust Z-scores for the last available visit for each subject. The aMCI/AD group was defined as those participants whose adjusted $Z_{mem}$ was 1 IQR below the median at their last available visit, i.e., $Z_{mem}$(last)$\leq -1.35$. Converters were defined as that subset of the a MCI/AD group whose adjusted $Z_{mem}$ at baseline visit 0 was no more than 1 IQR below the median, i.e., $Z_{mem}$(visit=0)>$-1.35$ and $Z_{mem}$(last)$\leq -1.35$. Participants were classified as NC if they had central scores on all domains at both the first and last visits, i.e., only if they met all of the following six conditions: (i) $-1 < Z_{mem}$(last)$<1$, (ii) $-1 < Z_{mem}$(visit=0)$<1$, (iii) $Z_{min}$(last)>$-1.35$, (iv) $Z_{min}$(visit=0)>$-1.35$, (v) $Z_{max}$(last)$<1.35$, and (vi) $Z_{max}$(visit=0)$<1.35$, where $Z_{max}$(last) and $Z_{max}$(visit=0) denote the maximum of the five adjusted Z-scores at the last and first visits, respectively. $Z_{mem}$ for normal participants had to be within 0.74 IQR (1 SD) of the median, rather than just 1 IQR (1.35 SD), to guarantee that they were >0.25 IQR (0.35 SD) from aMCI/AD participants.

After three years of being in the study, (December, 2010), 202 participants had completed a baseline and two yearly visits. At the third visit, 53 participants met criteria for aMCI/AD and 96 met criteria for NC. Of the 53 aMCI/AD participants, 18 were Converters and 35 were incident aMCI or AD. The remaining 53 participants did not meet the criteria for either group and were not considered for biomarker profiling. Some of these individuals met criteria for non-amnestic MCI and many had borderline or even above average memory scores that precluded their inclusion as either aMCI/AD or NC. 53 of the NC participants were matched to the 53 aMCI/AD participants based on sex, age, and education level. Blood samples were obtained on the last available study visit for the 53 MCI/AD and the 53 NC for biomarker discovery. Two blood samples from each of the 18 Converters were also included: one from the baseline visit ($C_{pre}$) when $Z_{mem}$ was non-impaired and one from the third visit ($C_{post}$) when $Z_{mem}$ was impaired and they met criteria for either aMCI or AD. Thus, at total of 124 samples from 106 participants were analyzed.

Internal cross-validation was employed to validate findings from the discovery phase. Blood samples for validation were identified at the end of the fifth year of the study and all 106 participants included in the discovery phase were excluded from consideration for the validation phase. Cognitive composite Z-scores were re-calculated based on the entire sample available and the same procedure and criteria were used to identify samples for the validation phase. A total of 145 participants met criteria for a group: 21aMCI/AD and 124 NC. Of the 21 aMCI/AD, 10 were Converters. 20 of the NC participants were matched to the aMCI/AD participants on the basis of age, sex, and education level as in the discovery phase. In total, 41 participants contributed samples to the validation phase and, as before, the 10 Converters also contributed a baseline sample ($C_{pre}$) for a total of 51 samples.

Neurocognitive Statistical Analyses

The neurocognitive analyses were designed to demonstrate the general equivalence of the discovery and validation samples on clinical and cognitive measures. Separate Multivariate Analysis of Variance (MANOVA's) tests were used to examine discovery/validation group performance on the composite Z-scores and on self-report measures of memory complaints, memory related functional impairment, depressive symptoms, and a global measure of cognitive function. In the first MANOVA, biomarker sample (discovery, validation) was the independent variable and MMQ, IADL, GDS, and MMSE were the dependent variables. In the second MANOVA, biomarker sample (discovery, validation) was the independent variable and the five cognitive domain Z-scores ($Z_{att}$, $Z_{exe}$, $Z_{lan}$, $Z_{mem}$, and $Z_{vis}$) were the dependent variables. Significance was set at alpha=0.05 and Tukey's HSD procedure was used for post-hoc comparisons. All statistical analyses were performed using SPSS (version 21).

Example 2

Sample Extraction Methods for Gene Expression Analysis

Blood was drawn from the subjects and placed in a PAXgene® blood tube (Qiagen). Samples were then processed according to the manufacturer's suggested protocol for RNA extraction.

Messenger RNA (mRNA) sequencing was performed using an Illumina HIGH SEQ™ high-throughput sequencing platform. In brief, after specimen thawing, globin mRNA was depleted from the total RNA samples using the GLOBINCLEAR™-Human Kit, which is a kit that removes alpha and beta globin mRNA from total RNA (# AM1980, Life Technologies, Grand Island, N.Y., USA), as described by the vendor. A total of 1.25 µg of RNA isolated from whole blood was then combined with biotinylated capture oligonucleotides complementary to globin mRNAs. The mixture was incubated at 50° C. for 15 minutes to allow duplex formation. Streptavidin magnetic beads were added to each specimen, and the resulting mixture was incubated for an additional 30 minutes at 50° C. to allow binding of the biotin moieties by Streptavidin. These complexes, comprising Streptavidin magnetic beads bound to biotinylated capture oligonucleotides that are specifically hybridized to the specimen globin mRNAs, were then separated from the solution using a magnet. The globin-depleted supernatant was transferred to a new container and further purified using RNA binding beads. The final globin mRNA-depleted RNA samples were quantified using a NANODROP ND 8000™ spectrophotometer (Thermo Fisher Scientific, Inc., Waltham, Mass., USA).

Libraries were prepared for RNA-Seq using the TRUSEQ™, an RNA Sample Prep Kit (Illumina, Inc., San Diego, Calif., USA), including the use of Illumina in-line control spike-in transcripts. Prior to library preparation, RNA samples were quantitated by spectrophotometry using a NANODROP ND 8000™ spectrophotometer, and assessed for RNA integrity using an Agilent 2100 BIOANALYZER™ electrophoresis machine (Agilent Technologies Inc., Santa Clara, Calif., USA) or Caliper LABCHIP GX™ electrophoresis machine (PerkinElmer, Waltham, Mass., USA). RNA samples with A260/A280 ratios ranging from 1.6-2.2, with RIN values ≥7.0, and for which at least 500 ng of total RNA proceeded to library preparation.

Library preparation was initiated with 500 ng of RNA in 50 µl of nuclease-free water, which was subjected to poly (A)+ purification using oligo-dT magnetic beads. After washing and elution, the polyadenylated RNA was fragmented to a median size of ~150 bp and then used as a template for reverse transcription. The resulting single-stranded cDNA was converted to double-stranded cDNA; ends were repaired to create blunt ends, and then a single A residue was added to the 3' ends to create A-tailed molecules. Illumina indexed sequencing adapters were then ligated to the A-tailed double-stranded cDNA. A single index was used for each sample. The adapter-ligated cDNA was then subjected to PCR amplification for 15 cycles. This final library product was purified using AMPURE™ beads (Beckman Coulter, Inc., Pasedena, Calif., USA), quantified by qPCR (Kapa Biosystems, Inc., Wilmington, Mass., USA), and its size distribution assessed using an Agilent 2100 BIOANALYZER™ electrophoresis machine or Caliper LABCHIP GX™ electrophoresis machine. Following quantitation, an aliquot of the library was normalized to 2 nM concentration and equal volumes of specific libraries were mixed to create multiplexed pools in preparation for Illumina sequencing.

RNA-Seq analysis included the data files FASTQ, BAM, translated CEL, quality control and summary. Transcript level differentially expressed gene (DEG) analysis, using the BAM files for input, was conducted using EdgeR package in Bioconductor as described in Robinson, M. D., et al. Bioinformatics 26, 139-140 (2010), which is incorporated by reference. A General Linear Model was used in EdgeR to compare groups of samples with multiple testing corrections performed using FDR with significance threshold set at 0.1 (10% FDR). Log 2 transformed read counts for differentially expressed transcripts were further analyzed at the gene level. Hierarchical clustering of DEGs, Heatmaps, and PCA analyses were performed using the TM4 software package as described in Saeed, A. I., et al., Methods Enzymol 411, 134-193 (2006), which is incorporated by reference. DEGs were subjected to downstream systems biology analysis using pathway enrichment analysis, Gene Ontology enrichment, and gene network enrichment analysis based on the Fisher's exact test (Ingenuity IPA [Ingenuity® Systems, www.ingenuity.com] as described in Jimenez-Marin, A., et al., BMC Proceedings 3 Suppl 4, S6 (2009) which is incorporated by reference, and Pathway Studio™ software packages [Elsevier, www.elsevier.com] as described Nikitin, A., et al., Bioinformatics 19, 2155-2157 (2003) which is incorporated by reference. In addition variant analysis was performed as described in Wang, K., et al., Nucleic Acids Res 38, e164 (2010), which is incorporated by reference. Sample classification was performed using R based machine learning algorithms of Support Vector Machine with recursive feature elimination (SVM-RFE) and 2-fold cross validation as described in Guyon, I., et al., Machine Learning 46, 389-422 (2002), which is incorporated by reference.

For each group comparison a minimal number of features that provided maximum accuracy of classification (as determined by SVM-RFE) was used to generate Receiver Operating Characteristic (ROC) curves. ROC curves were generated for each data type with 95% confidence intervals using the R package pROC as described in Robin, X., et al, BMC Bioinformatics 12, 77 (2011) which is incorporated by reference: an open-source package for R to analyze ROC curves (Bioconductor). Leave-one-out cross validation was used to validate the results of ROC analysis and the bootstrapping option was used to generate confidence intervals. Overfitting can be a significant problem when global profiling data are used to classify samples. In this analysis this problem was addressed by applying a multi-step data reduction, feature ranking, and various cross-validation procedures to each dataset. First, data was pre-filtered on significance of differences, which led to a significant reduction in the number of features. Second, we the RFE algorithm was applied in conjunction with SVM for each group comparison that allowed ranking the features and selecting a minimal number of features allowing for maximum classification accuracy. SVM-RFE algorithm has been reported in the literature as one of the best classification algorithms for addressing overfitting issues in gene expression analysis. See Guyon, I., et al, Machine Learning 46, 389-422 (2002), which is incorporated by reference. For each data type this algorithm was applied with rigorous cross-validation procedures: at each step in SVM-RFE a 2-fold cross-validation was used with 10,000 permutations (a variation of k-fold cross-validation). For each fold, data points were randomly assigned to two sets, d0 and d1 (which were implemented by shuffling the data array and then splitting it in two), which were then used to train on d0 and test on d1, followed by training on d1 and testing on d0. This 2-fold cross-validation method has the advantage that the training and test sets are both large compared with k-fold cross-validation, and each data point is used for both training and validation on each fold as described by Arlot, S and Cellise, A., Statistics Surveys 4, 40-79 (2010) and Picard, R., and Cook, R., Journal of the American Statistical Soiety 79, 575-583 (1984), which are incorporated by reference. After this step the number of features for each data set was already reduced 5 to 10 fold. Third, the ROC was calculated for each set of minimal number of features (that provided maximum accuracy of classification) and validated using leave-one-out cross-validation procedure. Finally, the confidence intervals for ROC curves were estimated using the bootstrapping approach. Overall, the problem of overfitting was directly addressed in this analysis by multiple computational procedures of feature reduction, ranking, elimination, and cross-validation that were applied consecutively for each dataset.

Differential Gene Expression Analysis

Once the RNA transcripts were sequenced, levels of each transcript were quantified as described above. These levels were then assessed to determine if a specific set of genes in $C_{pre}$ subjects was differentially expressed compared to normal subjects.

The same statistical regularized learning technique that was utilized for development of the 10 lipid panel (Mapstone, M., et al. Nat Med., 20(4):415-418; doi: 10.1038/nm.3466 (2014), which is incorporated by reference) was also used to discover the panel of differentially expressed genes (DEGs). The method used a receiver operating characteristic (ROC) regularized learning technique (Ma, S. & Huang, J., Bioinformatics 21, 4356-4362 (2005) and Liu, Z. & Tan, M., Biometrics, 64: 1155-1161 (2008), which are incorporated by reference). The technique is based on the least absolute shrinkage and selection operator (LASSO) penalty (Tibshirani, R., Journal of the Royal Statistical Society, Series B (Methodological 58, 267-288 (1996) and Hastie, T., et al., The Elements of Statistical Learning; Data Mining, Inference, and Prediction, (Springer-Verlag, New York, 2008), which are incorporated by reference). The LASSO penalty is implemented with the R package 'glmnet' (Friedman, J., et al., Journal of Statistical Software, 33: 1-22 (2010), incorporated by reference), which uses cyclical coordinate descent in a path-wise fashion. The least number of DEGs that provided the most significant AUC values were selected.

What is claimed is:

1. A method of treating a patient who has an increased risk of memory impairment, the method comprising a) determining whether the patient has an increased risk of memory impairment by analyzing at least one sample from the patient prior to the onset of memory impairment to determine patient's gene expression levels of a set of genes, wherein the set of genes comprises SART3, SMARCB1, EXO1, CKAP2L, RGPD3, RBFOX2, SKIL, STYX, SORBS2, LYPLA1, CHGA, PXDNL, SGMS2, OBSCN, RAPGEF3, SPRY2, FAM98C, ABLIM3, MARCH4, SCLY, GATAD2A, STAG2, DTNA, HSD17B4 and PML and b) administering a treatment for memory impairment to the patient when the patient is determined to have an increased risk of memory impairment;

wherein the patient is determined to have an increased risk of memory impairment when the patient's gene expression levels are altered from gene expression levels obtained from one or more subjects determined to define normal gene expression levels, wherein (i) the expression levels of the genes SART3, SMARCB1, EXO1, CKAP2L, RGPD2, RBFOX2, SORBS2, CHGA, PXDNL, RAPGEF3, MARCH4, GATAD2A are lower than normal gene expression levels, and (ii) the expression levels of the genes SKIL, STYX, LYPLA1, SGMS2, OBSCN, SPRY2, FAM98C, ABLIM3, SCLY, STAG2, DTNA, HSD17B4, PML are higher than normal gene expression levels.

2. The method of claim 1, wherein the normal gene expression profile obtained from one or more subjects comprises the patient's gene expression profile prior to the onset of memory impairment and prior to analyzing the at least one sample in step (a).

3. The method of claim 1, wherein the normal gene expression profile obtained from one or more subjects comprises a gene expression profile generated from a population of individuals that have never displayed memory impairment.

4. The method of claim 1, wherein the treatment is administered to subject prior to the onset of any detectable signs of memory impairment in the patient.

5. The method of claim 1, wherein the sample is a plasma sample.

* * * * *